United States Patent [19]

Tovey et al.

[11] 4,426,455

[45] Jan. 17, 1984

[54] ASSAY OF VITAMIN B12

[75] Inventors: Keith C. Tovey; David T. Carrick, both of Amersham, England

[73] Assignee: Amersham International Limited, England

[21] Appl. No.: 300,979

[22] Filed: Sep. 9, 1981

[30] Foreign Application Priority Data

Sep. 22, 1980 [GB] United Kingdom ................ 8030544

[51] Int. Cl.$^3$ .................... G01N 33/54; G01N 33/56; G01N 33/58
[52] U.S. Cl. ..................................... 436/505; 436/825
[58] Field of Search ..................... 424/1; 436/504, 505

[56] References Cited

U.S. PATENT DOCUMENTS

| 4,028,465 | 6/1977 | Lewin et al. | 436/505 |
| 4,279,859 | 7/1981 | Gutcho et al. | 424/1 |
| 4,332,786 | 6/1982 | Cabelli et al. | 424/1 |

Primary Examiner—Christine M. Nucker
Attorney, Agent, or Firm—Wenderoth, Lind & Ponack

[57] ABSTRACT

A method of assaying for vitamin B12 achieves denaturation of serum binding proteins which normally bind the vitamin B12 by treatment with alkali at ambient temperature. The assay is characterized by the use, in the alkali denaturation step, of a dithiopolyol and cyanide, and by the use, during the intrinsic factor assay step, of a vitamin B12 analogue such as cobinamide to bind with any remaining serum proteins. The invention also includes a kit, in which the dithiopolyol is provided in admixture with the alkali.

10 Claims, No Drawings

ASSAY OF VITAMIN B12

Serum B12 bound to carrier protein must be released before it can be assayed. Conventional methods involve heating the serum for 15-30 minutes in the presence of cyanide. In assays carried out in large clinical chemistry laboratories, any heating process is unwelcome as interrupting the flow of the work. A heating process which, because of the presence of cyanide (especially if in acid solution) requires the use of a fume cupboard, is highly undesirable.

An article in Clinical Chemistry, volume 26, No.2, 1980, pages 323-6, proposes an assay in which endogenous serum B12 is released from its protein complexes at room temperature with NaOH at pH 13.6. But the protocol involves using very large concentrations of cyanide (2000 micrograms/ml of serum) in the denaturation step. Also, oyster toadfish serum is used as the specific reagent for vitamin B12 in place of the more usual porcine intrinsic factor. So far as is known, this assay has not been used commercially. There is a clearly identified and long-felt need for an assay for vitamin B12 using intrinsic factor, in which serum binding proteins are denatured without the use of heat or of large concentrations of cyanide.

It is known that dithiopolyols such as dithiothreitol (DTT) can help in releasing vitamin B12 from serum binding proteins. An article in the American Journal of Clinical Pathology, August 1980, volume 74, No.2, pages 209-213 compares three commercial vitamin B12 assay kits in which denaturation of serum proteins is effected by boiling. A problem of non-specific binding associated with one of the kits was dealt with by including DTT and cobinamide with the other assay ingredients.

The present invention provides a method of assaying for vitamin B12 in serum comprising the steps:
(a) Mixing a sample of the serum to be assayed with alkali, cyanide, and a dithiopolyol having from 4 to 6 carbon atoms,
(b) incubating the mixture at a temperature not exceeding 50° C. for a time sufficient to separate the vitamin B12 from serum binding proteins and to substantially denature the proteins,
(c) providing in the mixture, either before, during or after performing step (b), a standard amount of radioactively labelled vitamin B12, and a vitamin B12 analogue which binds strongly to serum binding proteins of the sample but not to intrinsic factor,
(d) reducing the pH of the incubated mixture from step (b), adding thereto a standard amount, insufficient to bind all the vitamin B12 in the sample and the radioactively labelled vitamin B12, of intrinsic factor, and
(e) incubating the mixture to cause a fraction of the vitamin B12 in the sample and a fraction of the radioactively labelled vitamin B12 to become bound to the intrinsic factor, separating the bound fraction from the fraction not so bound, measuring the level of radioactivity of at least one fraction, and using the measurement to determine the concentration of vitamin B12 in the sample.

A feature of this invention is the inclusion of a dithiopolyol having from 4 to 6 carbon atoms in step (a) to assist separation of the vitamin B12 from serum binding proteins. Preferred dithiopolyols are 1,4-dithiotetritols, including both of the isomers dithiothreitol and dithioerythritol. These are preferably used in proportions of 2-20, particularly 4-10, milligrams per milliliter of serum sample.

A further feature of the invention is the use of cyanide in step (a). Cyanide converts the various cobalamins present to cyanocobalamins. It is believed that the dithiopolyol assists in the release of cyanocobalamins from serum binding proteins. Dithiopolyols are particularly effective in the presence of cyanide, which suggests that they may be better able to release cyanocobalamins than other cobalamins from serum binding proteins. Our preferred cyanide concentration is from 10-1000, particularly from 20-200, micrograms per milliliter of serum sample.

Cyanide and dithiopolyols assist in separating vitamin B12 from serum binding proteins, but do not themselves denature the proteins. Accordingly, when the pH is reduced in step (d), there is a danger that the serum binding proteins may to some extent re-combine with the vitamin B12. According to a further feature of this invention, this danger is avoided by incorporating in the mixture at step (c) a vitamin B12 analogue which binds to any remaining undenatured serum binding proteins of the sample, but not to the added intrinsic factor. The amount of the vitamin B12 analogue used should be at least enough to occupy all the binding sites of the undenatured serum binding proteins to the sample, and is preferably from 10-1000 times the amount required to occupy all the said binding sites. A suitable vitamin B12 analogue is cobinamide, which binds strongly to serum binding proteins but hardly at all to intrinsic factor. Other vitamin B12 analogues may be used.

In step (b), the separation and partial denaturing of the serum binding proteins is performed at a temperature not above 50° C. and preferably at ambient temperature. The pH of the sample should be at least 12.0, preferably 12.5-13.7, particularly 12.9-13.5. The alkali, which may conveniently be sodium hydroxide, is used in an amount to achieve the desired pH. The time required for reaction is generally from 5-60 minutes, typically about 15 minutes, and can readily be determined by trial and error.

In step (e), the mixture of treated sample and intrinsic factor is incubated under conditions of pH and temperature at which the intrinsic factor strongly binds vitamin B12. These conditions may be pH 9.3 at ambient temperature.

The vitamin B12 tracer may conveniently be labelled with cobalt-57. The tracer may be added to the serum sample either before, during or after step (b). It may be convenient to provide a single reagent containing labelled vitamin B12 and cyanide for addition to the sample in step (a).

The vitamin B12 analogue, e.g. cobinamide, may be added before, during or after step (b). Preferably it is added after step (b). It may be convenient to provide a single reagent containing cobinamide and intrinsic factor in step (d).

Dithiopolyol stability has always been a problem. In one commercial vitamin B12 assay kit, DTT is supplied as an aqueous solution which may be stored at 4° C. for up to 30 days after opening the vial. Before use the DTT solution is mixed with the radioactive tracer to give a working tracer solution which is stable only for a day. In another commercial kit DTT is supplied as a freeze-dried powder which can be stored as such at 2°-8° C. After reconstitution it must be stored at minus 20° C. Before use it is mixed with the labelled vitamin B12 to give a working tracer solution.

A further feature of the present invention is that the dithiopolyol may be provided in admixture with the alkali used to denature the serum proteins. This is unexpected, because it has long been well known that mercaptans are readily oxidised to disulphide by air, especially in alkaline solution. Our assay which does not work without a dithiopolyol, works entirely satisfactorily with solutions of DTT in NaOH which has been stored for upwards of 14 weeks at 2°–4° C., or which have been stored for up to 2 weeks at 37° C.

The invention therefore further provides a kit for performing an assay of vitamin B12 in serum comprising supplies of alkali, a dithiopolyol having 4–6 carbon atoms, cyanide, radioactively labelled vitamin B12, intrinsic factor, and a vitamin B12 analogue which binds strongly to serum binding proteins in serum but not to intrinsic factor, wherein the supplies of alkali and dithiopolyol are provided in admixture.

It is quite usual to perform a dual assay for vitamin B12 and folate, by adding cobalt-57 labelled vitamin B12 and iodine-125 or iodine-131 labelled folate and specific binding proteins for both materials, to the same serum sample. The method of the present invention of assaying for vitamin B12 may advantageously be carried out together with an assay for folate. Folate is normally present in serum together with folate binding proteins. Step (b) of the method of the present invention, performed at low temperature to remove serum binding proteins, has no deleterious effect on the folate assay.

The source of the intrinsic factor is unimportant. Usually, human or porcine intrinsic factor will be used.

EXAMPLE 1

Reagents and protocol for an assay according to this invention.

Reagents
  (a) Standards contain vitamin B12 in calibrated quantities, buffer-based containing human serum albumin.
  (b) Tracer is $^{57}$Co-cyanocobalamin in a preserved 10 mM phosphate buffer containing 0.1% $^w$/v potassium cyanide.
  (c) Denaturation reagent is a 1.2 M sodium hydroxide solution containing 1.0% dithiothreitol.
  (d) Binding reagent is purified hog intrinsic factor in a preserved 0.2 M borate buffer containing human serum albumin and 20 micrograms per liter of cobinamide.
  (e) Charcoal tablets are a mixture of protein-coated charcoal with microcrystalline cellulose in a weight ratio of 1:3.

Assay Procedure
  1. Label and arrange the assay tubes in racks according to the protocol shown in Table 1.
  2. Pipette 200 μl aliquots of the standards, and unknown sera into the appropriate tubes using a fresh pipette tip for each new solution.
  3. Pipette 100 μl aliquots of tracer into all the tubes.
  4. Pipette 100 μl aliquots of denaturation reagent into all tubes.
  5. Vortex mix all the tubes thoroughly ensuring that no drops of unmixed reagent remain. Cover the tubes with a tissue and incubate in subdued light for 15 minutes at room temperature.
  6. Pipette 1000 μl of binding reagent into all the tubes except the totals and blank tubes. Pipette 1000 μl of distilled water into the totals and blank tubes.
  7. Vortex mix all tubes thoroughly and incubate for 45 minutes at room temperature in subdued light.
  8. At the end of the incubation period use a pair of forceps to add 1 charcoal tablet to each tube except the totals.
  9. Allow the tablets to disintegrate for at least 5–10 seconds. Vortex for 1–2 seconds, remove and immediately vortex again for an additional 6–10 seconds (see Note 6).
  10. Allow all the tubes to incubate at room temperature for 15 minutes.
  11. Centrifuge all tubes (except totals) for at least 10 mins at 1500 g. The free vitamin B12 is adsorbed by the charcoal; the bound vitamin B12 remains in the supernatant.
  12. After centrifugation, decant the supernatants into a clean set of labelled tubes, tap the rims of the tubes together to obtain complete transfer of supernatant.
  13. Count all the tubes in a suitably programmed gamma counter for 60 seconds or for at least 10,000 counts in tubes 5–6.

Results
  1. Prepare 2 standard curves on log/linear graph paper by plotting the counts per unit time on the linear axis against the concentration of vitamin B12 on folate on the log axis. Construct the best standard curves through the mean of duplicate points rejecting grossly aberrant points.
  2. Using the mean of the counts for the unknowns read off their vitamin B12 and folate concentrations from the respective standard curve.

The above assay was compared to a leading commercial assay kit (of the kind which requires boiling the sample to effect denaturation) and to a conventional microbiological assay (of the kind which is accepted as giving an accurate determination but is too slow and cumbersome for routine clinical use). In both cases a linear correlation was found with a high correlation coefficient above 0.94. This demonstrates that the assay of the present invention achieves accurate results without suffering from the disadvantages of existing assays, namely the need to boil the sample in alkali with cyanide to denature the serum proteins.

TABLE I

| | ASSAY PROTOCOL | | | | | | | | UNKNOWNS. | |
| | | | STANDARDS. | | | | | | | |
| Tube Nos. | TOTALS 1–2 | BLANK 3–4 | 0 5–6 | 50 7–8 | 150 9–10 | 400 11–12 | 1000 13–14 | 2000 15–16 | 1 | 2 etc |
|---|---|---|---|---|---|---|---|---|---|---|
| Standards | — | 200 | 200 | 200 | 200 | 200 | 200 | 200 | — | — |
| Controls or unknowns | — | — | — | — | — | — | — | — | 200 | 200 |
| Dual tracer | 100 | 100 | 100 | 100 | 100 | 100 | 100 | 100 | 100 | 100 |
| Denaturation reagent | — | 100 | 100 | 100 | 100 | 100 | 100 | 100 | 100 | 100 |
| | | | Vortex mix. Incubate for 15 minutes at room temperature. | | | | | | | |
| Binding Protein | — | — | 1000 | 1000 | 1000 | 1000 | 1000 | 1000 | 1000 | 1000 |

TABLE I-continued

| Tube Nos. | ASSAY PROTOCOL | | | | | | | | UNKNOWNS. | |
| --- | --- | --- | --- | --- | --- | --- | --- | --- | --- | --- |
| | | | STANDARDS. | | | | | | | |
| | TOTALS 1-2 | BLANK 3-4 | 0 5-6 | 50 7-8 | 150 9-10 | 400 11-12 | 1000 13-14 | 2000 15-16 | 1 | 2 etc |
| Solution Water | 1000 | 1000 | — | — | — | — | — | — | — | — |

Vortex mix. Incubate for 45 minutes at room temperature.

Add 1 charcoal tablet to all tubes (except totals), vortex 1-2 seconds, remove and vortex for a further 6-10 seconds.
Incubate all tubes for 15 minutes at room temperature.
Centrifuge all tubes at 1500 g for 10 minutes. Decant the supernatants into a clean set of labelled tubes and count.

Note:
All volumes are in microliters

EXAMPLE 2

The following reagents and procedures were used to determine the serum blanks (non-specific binding of vitamin B12) obtained under various conditions in the alkaline denaturation step of the vitamin B12 assay. It is evident, from the data subsequently presented, that uniquely defined conditions are necessary for the effective denaturation, with sodium hydroxide, of vitamin B12 binding proteins in human serum.

Reagents
1a. 1.5 N sodium hydroxide.
1b. Distilled water.
Tracer Solution
2a. 1.5 µCi ($^{57}$Co) vitamin B12 tracer in potassium phosphate buffer containing human serum albumin and preservative.
2b. As 2a but containing also KCN (0.5 mg/ml).
2c. As 2a but containing also dithiothreitol (1% w/v).
2d. As 2a but containing also KCN (0.5 mg/ml) and dithiothreitol (1% w/v) assay solution.
3a. Sodium borate buffer pH 7.2 containing human serum albumin, and sodium chloride.
3b. As 3a but containing also dithiothreitol (0.1% w/v).
3c. As 3a but containing also KCN (50 µg/ml).
3d. As 3a but containing also dithiothreitol (0.1% w/v), and KCN (50 µg/ml).
3e. As 3a but containing also cobinamide (20 ng/ml).
4. Protein coated charcoal suspension in 0.9% (w/v) sodium chloride solution containing preservative (75 mg charcoal/ml).

| Procedure for determination of serum non-specific binding | | | | | | | | |
| --- | --- | --- | --- | --- | --- | --- | --- | --- |
| | Assay Conditions | | | | | | | Total Counts Tubes |
| | 1 | 2 | 3 | 4 | 5 | 6 | 7 | |
| Add 200 µl of serum* | → | → | → | → | → | → | → | → |
| Add 100 µl of reagent | 2a | 2d | 2a | 2b | 2c | 2d | 2d | 2a |
| Add 100 µl of reagent | 1b | 1a | 1a | 1a | 1a | 1a | 1a | 1a |
| Add 1000 µl of reagent | — | 3a | — | — | — | — | — | — |
| Vortex mix and incubate for 15 minutes at ambient temperature (except the tubes in assay condition 2 which are incubated for 15 minutes at 100° C.). | | | | | | | | |
| Add 1000 µl of reagent | 3a | — | 3d | 3b | 3c | 3a | 3e | 3a |
| Vortex mix and incubate for 45 minutes at ambient temperature | | | | | | | | |
| Add 200 µl of reagent | 4 | 4 | 4 | 4 | 4 | 4 | 4 | — |
| Vortex mix and stand for 5 minutes. Centrifuge all tubes except totals at 1500 g for 10 minutes, decant supernatants into a clean set of labelled tubes. Count all supernatants and the whole content of the total tubes in a gamma counter. | | | | | | | | |

*Twelve human serum samples were tested under each condition.

Results
The results are set out in the following table. Figures are the mean counts obtained on twelve individual serum samples expressed as a percentage of the total counts.

Mean (n = 12) serum blank values obtained in the vitamin b12 assay under various conditions.

| Assay Conditions | Serum blank value (% non-specific binding) |
| --- | --- |
| 1. Assay without denaturation of endogenous binding proteins | 87.1 (±7.5) |
| 2. Assay with heat denaturation (boiling water bath) Alkaline denaturation: | 7.2 (±0.9) |
| 3. DTT and KCN present in assay solution (pH 9.3) | 23.7 (±3.2) |
| 4. KCN in tracer solution (pH 13). DTT present in assay solution (pH 9.3) | 28.9 (±3.0) |
| 5. DTT in tracer solution (pH 13). KCN present in assay solution (pH 9.3) | 15.6 (±3.4) |
| 6. DTT and KCN in tracer solution (pH 13) | 8.9 (±0.8) |
| 7. DTT and KCN in tracer solution (pH 13) 20ng/ml of cobinamide present in assay solution (pH 9.3) | 4.3 (±0.4) |

Discussion

Condition 1, where there was no denaturing step, shows that the bulk of vitamin B12 is present in serum in bound form. In condition 2, denaturing was effected by boiling with cyanide, an inconvenient step but one which reduced the non-specific binding to an acceptable value. Room temperature denaturation, with or without cyanide (condition 4 and 3) left 20-30% of the vitamin B12 bound to non-specific serum proteins. Room temperature denaturation in the presence of dithiothreitol (condition 5) produced better results, and these were greatly further improved when cyanide was also added prior to denaturing (condition 6). The result of condition 6 was yet further improved when cobinamide was present in the assay solution (condition 7).

The results of condition 2, 6 and 7 were all acceptable from a standpoint of accuracy, but condition 6 and 7 had the great advantage over condition 2 that the results were achieved using ambient temperatures only.

We claim:
1. A method of assaying for vitamin $B_{12}$ in serum comprising the steps
  (a) mixing a sample of the serum to be assayed with alkali, cyanide, and a dithiopolyol having from 4 to 6 carbon atoms.

(b) incubating the mixture at a pH of at least 12 and a temperature not exceeding 50° C. for a time sufficient to separate the vitamin $B_{12}$ from serum binding proteins and to substantially denature the proteins, (c) providing in the mixture, either before, during or after performing step (b), a standard amount of radioactively labelled vitamin $B_{12}$, and a vitamin $B_{12}$ analogue which binds strongly to serum binding proteins of the sample but not to intrinsic factor, (d) reducing the pH of the incubated mixture from step (b), adding thereto a standard amount, insufficient to bind all the vitamin $B_{12}$ in the sample and the radioactively labelled vitamin $B_{12}$, of intrinsic factor, and (e) incubating the mixture to cause a fraction of the vitamin $B_{12}$ in the sample and a fraction of the radioactively labelled vitamin $B_{12}$ to become bound to the intrinsic factor, separating the bound fraction from the fraction not so bound, measuring the level of radioactivity of at least one fraction, and using the measurement to determine the concentration of vitamin $B_{12}$ in the sample.

2. A method as claimed in claim 1, wherein in step (a) the alkali and the dithiopolyol are added as a preformed mixture to the serum sample.

3. A method as claimed in claim 1, wherein the dithiopolyol is dithiothreitol or dithioerythritol.

4. A method as claimed in claim 1, wherein the vitamin B12 analogue is cobinamide.

5. A method as claimed in claim 1, wherein cyanide is used in step (a) in an amount equivalent to 20 to 200 μg of potassium cyanide/ml of serum.

6. A method as claimed in claim 1, wherein the dithiopolyol is used in step (a) in an amount of from 4 to 10 mg/ml of serum.

7. A method as claimed in claim 1, wherein the vitamin B12 analogue is used in an amount of from 10 to 1000 times that required to occupy all the binding sites of the serum binding proteins which have not been denatured by the step (b) incubation.

8. A kit for performing an assay of vitamin B12 in serum comprising supplies of alkali, a dithiopolyol having 4 to 6 carbon atoms, cyanide, radioactively labelled vitamin B12, intrinsic factor, and a vitamin B12 analogue which binds strongly to serum binding proteins in serum but not to intrinsic factor, wherein the supplies of alkali and dithiopolyol are provided in admixture.

9. A kit as claimed in claim 8, wherein the supplies of radioactively labelled vitamin B12 and cyanide are provided in admixture.

10. A kit as claimed in claim 8, wherein the vitamin B12 analogue is cobinamide.

* * * * *